United States Patent [19]

Kocmich

[11] 4,000,640
[45] Jan. 4, 1977

[54] TONOMETER TESTER
[75] Inventor: Donald Orrie Kocmich, Hillsborough, Calif.
[73] Assignee: Opti Products Incorporated, Reno, Nev.
[22] Filed: Aug. 8, 1975
[21] Appl. No.: 603,192
[52] U.S. Cl. .................................. 73/1 B; 128/2 T
[51] Int. Cl.² ...................................... G01L 25/00
[58] Field of Search ................. 73/1 B, 4 R, 80; 128/2 T

[56] References Cited
UNITED STATES PATENTS

| 585,883 | 7/1897 | Bosworth | 73/4 |
| 1,699,812 | 1/1929 | Sartakoff | 73/4 |
| 3,736,789 | 6/1973 | Drew | 73/1 |
| 3,889,518 | 6/1975 | DeNouter | 73/4 |

FOREIGN PATENTS OR APPLICATIONS

| 91,723 | 2/1921 | Switzerland |

OTHER PUBLICATIONS

Freid et al., "The F–B Cornea Tonometer Calibration Device" in J. Optom. & Archives of Am. Acad. of Optom., vol. 49, No. 2, Feb. '72, pp. 96–105.

Primary Examiner—Herbert Goldstein

[57] ABSTRACT

A device which is designed to test applanation type tonometers. The device includes a reservoir to maintain a constant liquid level mounted on top of a liquid filled vertical column having multiple connections with outlet means closed by thin membranes with characteristics so that a known liquid pressure deforms the membrane in a bulbous shape approximating the contour of the human eye which thus provides said device with the means for testing applanation type tonometers.

1 Claim, 3 Drawing Figures

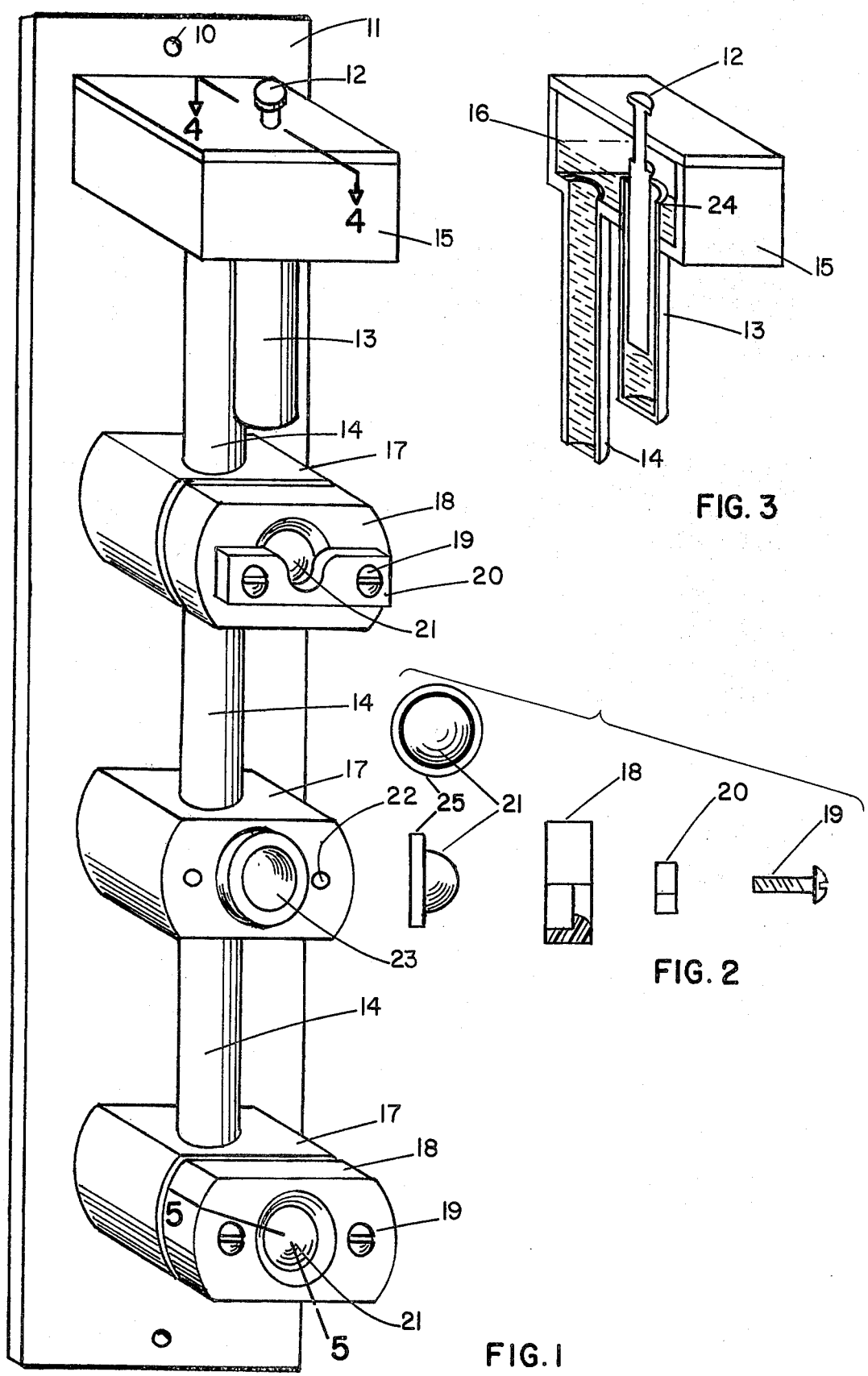

TONOMETER TESTER

Tonometers are used to measure pressure within the eyeball and a usual procedure to establish pressure range for the tonometer settings is to use gravitational force to act upon the probe sensor element. If there is friction in the probe sensor element, the dial settings can be in error.

There are procedures that use electronic pressure measuring equipment to directly measure the pressure of the aqueous humor in the eye and compare the data as shown on the tonometer. This equipment is costly and time consuming to operate. Various forms of manometers and pressure gauges can be used to measure pressure but pressure must be developed on separate equipment and the equipment is time consuming to use. The present invention overcomes these objections and its merit will be apparent in the following description:

It is an object of the present invention to provide an improved device for creating multiple known pressures simultaneously.

It is another object of the present invention to provide an improved tonometer tester.

It is another object of the present invention to make the tonometer tester easy to use after the tonometer has been used to check a patient's eye.

The present invention uses a reservoir, with a constant liquid level maintained in the reservoir, mounted on top of a column. The column is filled with liquid and has multiple connections with outlet means spaced along the vertical column. As all connections are simultaneously subject to liquid pressure, the device can be used to rapidly make a series of pressure tests.

If the outlet connections are closed with thin membranes of proper design, the pressure at the connection would form the membrane into a bulbous shape approximating the contour of the human eye. If a tonometer probe is properly guided into contact with the membrane, a simulated applanation tonometery results.

The present invention is compact enough to be portable and can easily be placed in convenient proximity to the applanation tonometer equipment. The ready availability of the tonometer tester with the multiple test points makes it easy to use, and the data from the test of a patient's eye can be compared with a maximum of reliability being achieved.

For a complete understanding of the invention, together with an appreciation of other objects and advantages there of, please refer to the following detailed description of the attached drawing in which:

FIG. 1 is a perspective view of the present invention.

FIG. 2 is an expanded sectional view showing the membrane housing taken along lines 5—5 of FIG. 1.

FIG. 3 is a cross sectional view of the reservoir taken along the lines 4—4 of FIG. 1.

FIG. 1 shows the perspective view of the device and includes a support 11, with mounting holes 10, supporting a reservoir containing liquid 15, that is attached to a liquid filled column 14 having multiple connections 17, spaced along column 14, each connection having outlet means 23, the outlet means being closed by a thin membrane 21, supported on an annular ring 25 of FIG. 2; the membrane normally is supported in the membrane housing 18, with screws 19 that attach the membrane housing 18 to the connection 17, and by means of the resilient annular ring achieve a liquid tight seal. The screws 19 can be used to locate and attach the probe guide 20 to the membrane housing 18. The reservoir containing liquid 15 of the present invention, provides accuracy to the invention by maintaining a constant liquid reference level because of its design, and as a result the liquid pressure developed at a connection is known and stable. This results in greater accuracy of measurement than the method now used to test a tonometer after the use of the tonometer on a patient's eye. Please refer to FIG. 3 showing a cross sectional view of the reservoir. The reservoir has two chambers, a primary chamber 16, having an area many times greater than the area of the column 14, and a secondary chamber 13, which normally receives the excess liquid from the primary chamber 16, as the opening at the top 24 of the secondary chamber 13, will determine the liquid level in the primary chamber 15; if the liquid level is low in the primary chamber 15, liquid can be transferred by pressing the displacement plunger 12, causing liquid to flow from the secondary chamber 13, into the primary chamber 15, to the proper level. The reservoir 15 and other parts of the device generally are constructed of transparent material so that the liquid in the device can be observed for entrapped gas. The connections 17, to the column 14, are made of similar material and can be made of machined or molded plastic such as acrylic with the complete assembly cemented together with various filler material that matches acrylic by a solvent method. The reservoir 15, is mounted on top of the column 14, having connections 17, spaced along the column 14; FIG. 1 shows three different connection variations:

The top connection 17, FIG. 1 has the following parts: membrane housing 18, with membrane 21 installed, probe guide 20, held in place with screws 19;

The middle connection 17, shows a open port 23;

The bottom connection 17, shows membrane housing 18 with membrane 21 installed, with the assembly being held together with screws 19.

One preferred form of the invention would have connections 17, at intervals that would be equivalent to pressures of 10, 20, 30, 40, millimeters of mercury. The pressure developed at the connections is a function of the specific gravity of the liquid in the device, multiplied by the head of liquid as measured from the level in the reservoir to the lowest point of the connection outlet means 23, thus each connection has a constant known pressure for reference purpose. When used to test tonometers, the connection outlets 23 are provided with thin membranes 21, to provide means of subjecting the sensor element of the tonometer probe to conditions that duplicate, as near as possible, the force and curvature and internal pressure of the eye. To produce the eye curvature, the membrane 21 is a part of an annular ring 25, FIG. 2 and the membrane thickness is tapered so that the thinnest section is in the center of the membrane 21. The liquid pressure forms the membrane 21 into a bulbous shape that can be controlled by varying the area of the membrane 21, acted upon by the liquid pressure.

The force acting against the sensor element of the tonometer probe is a function of the curvature of the membrane surface. The present invention has a further feature so that means is provided to guide 20, the sensitive element of a tonometer probe to engage the proper point of curvature of the surface of membrane 21.

The present invention speeds the procedure of checking the tonometer after use on a patient's eye, because the multiple test membranes provide reference forces that relate to known liquid pressures that can be quickly compared with the recorded data, thus the tonometer tester provides an improved test device.

While the invention is thus shown and a particular embodiment described in detail, it is not intended that the invention be limited to only the shown embodiment. Instead many modifications will occur to those skilled in the art which lie within the spirit and scope of the invention. For example the thin membrane could be altered with shaped surfaces thereby making the invention applicable to other than tonometer testing. It is thus intended that the invention be limited in scope only by the appended claims.

What is claimed is:

1. A device to provide multiple simultaneously known pressures and multiple pressurized test surfaces for the measurement of force comprising a vertical liquid filled column, a reservoir mounted on top of said column, means for providing a constant liquid level in said reservoir, multiple spaced housings, along the length of said column, each said housing having an internal cavity in fluid communication with said column and a flexible membrane lining at least a portion of said cavity, and having an exposed surface whereby said membrane, when subject to liquid pressure when within said cavity, forms a bulbous shape approximating the contour of the cornea of the human eye.

* * * * *